US010281378B2

(12) United States Patent
Wenski

(10) Patent No.: US 10,281,378 B2
(45) Date of Patent: May 7, 2019

(54) SYSTEM AND METHOD FOR TESTING TRUE STRESS AND TRUE STRAIN

(71) Applicant: HONEYWELL FEDERAL MANUFACTURING & TECHNOLOGIES LLC, Kansas City, MO (US)

(72) Inventor: Edward Wenski, Lenexa, KS (US)

(73) Assignee: Honeywell Federal Manufacturing & Technologies, LLC, Kansas City, MO (US)

(*) Notice: Subject to any disclaimer, the term of this patent is extended or adjusted under 35 U.S.C. 154(b) by 179 days.

(21) Appl. No.: 15/147,055

(22) Filed: May 5, 2016

(65) Prior Publication Data
US 2017/0322129 A1 Nov. 9, 2017

(51) Int. Cl.
G01N 3/06 (2006.01)
G01L 1/24 (2006.01)
H04N 5/225 (2006.01)
H04N 5/247 (2006.01)
G01M 11/08 (2006.01)
(Continued)

(52) U.S. Cl.
CPC ............. G01N 3/068 (2013.01); G01L 1/24 (2013.01); G01M 11/081 (2013.01); G01N 3/08 (2013.01); G06T 7/62 (2017.01); G01N 2203/0264 (2013.01); G01N 2203/0647 (2013.01); H04N 5/2256 (2013.01); H04N 5/247 (2013.01)

(58) Field of Classification Search
None
See application file for complete search history.

(56) References Cited

U.S. PATENT DOCUMENTS 2,645,151 A  12/1948 Hastings
4,418,563 A * 12/1983 Kalthoff .................. G01N 3/30
                                                    73/12.09
(Continued)

FOREIGN PATENT DOCUMENTS

CN  101319977  7/2008
CN  102221503  6/2011

OTHER PUBLICATIONS

Advanced Material Properties Measurements with Optical Metrology; Copyright 2011; SAE International.
(Continued)

Primary Examiner — Mohammad J Rahman
(74) Attorney, Agent, or Firm — Hovey Williams LLP

(57) ABSTRACT

A true stress testing system broadly comprising a force input machine, an imaging system, and a computer. The imaging system includes a light source for projecting a light beam at the specimen in a first direction and a camera positioned on an opposite side of the specimen for receiving portions of the light beam not blocked by the specimen such that a shadow image of the specimen is created via the camera. The computer may determine a minimum dimension of the specimen perpendicular to the first direction at a point in time over a plurality of points along the force axis via the shadow image of the specimen such that the processor accounts for changes in position of the minimum dimension along the specimen. A true stress of the specimen may then be determined according to the minimum dimension of the specimen perpendicular to the first direction at the point in time.

7 Claims, 5 Drawing Sheets

(51) Int. Cl.
*G01N 3/08* (2006.01)
*G06T 7/62* (2017.01)

(56) References Cited

U.S. PATENT DOCUMENTS

| | | | | |
|---|---|---|---|---|
| 4,491,763 A * | 1/1985 | Fujinuma | ............. | H01J 29/073 313/405 |
| 4,567,774 A * | 2/1986 | Manahan | ................. | G01N 3/00 374/49 |
| 4,724,012 A * | 2/1988 | Inaba | ..................... | C22C 38/40 148/327 |
| 6,930,685 B1 * | 8/2005 | Sakagawa | ............. | G06T 15/60 345/426 |
| 2003/0128337 A1 * | 7/2003 | Jaynes | .................. | G03B 21/26 353/30 |
| 2003/0182069 A1 * | 9/2003 | Banes | .................... | G01N 3/068 702/33 |
| 2004/0200293 A1 * | 10/2004 | Wenski | ................... | G01N 3/02 73/800 |
| 2004/0261911 A1 * | 12/2004 | Kondo | ................. | C22C 38/105 148/336 |
| 2006/0096385 A1 * | 5/2006 | Wenski | ................... | G01N 3/08 73/800 |
| 2007/0151359 A1 * | 7/2007 | Broadley | .............. | G01N 3/068 73/826 |
| 2008/0141783 A1 * | 6/2008 | Wong | .................... | G01N 3/307 73/844 |
| 2011/0292179 A1 * | 12/2011 | Hernandez | .......... | G01B 11/245 348/46 |
| 2012/0002898 A1 * | 1/2012 | Cote | ........................ | G06T 5/50 382/278 |
| 2012/0008021 A1 * | 1/2012 | Zhang | ................ | G06K 9/00791 348/251 |
| 2012/0314103 A1 * | 12/2012 | Majewicz | ............ | H04N 5/2354 348/239 |
| 2013/0143001 A1 * | 6/2013 | Manifold | ................ | D06C 23/04 428/167 |
| 2014/0375681 A1 * | 12/2014 | Robbins | ................ | G06T 19/006 345/633 |
| 2015/0009216 A1 * | 1/2015 | Watanabe | ............... | G06T 15/60 345/426 |
| 2015/0168303 A1 * | 6/2015 | Trupke | ............... | G01N 21/6456 324/762.01 |
| 2015/0276386 A1 * | 10/2015 | Keng | ..................... | G01B 11/16 356/32 |
| 2015/0377754 A1 * | 12/2015 | Kanade | ................. | G01N 3/068 73/788 |
| 2016/0299046 A1 * | 10/2016 | Xuan | ....................... | G01N 3/18 |

OTHER PUBLICATIONS

Measure Strain Distribution Using DIgital Image Crrelation (DIC) for Tensile Tests; Jan. 30, 2010; Dr. Lianxiang Yang (PI); Jr. Lorenzo Smith (Co-PI); Mr. Abhishek Gothekar (Graduate Student of Dr. Yang); Mr. Xu Chen (Graduate Student of Dr. Yang); Dept. of Mechanical Engineering; Oakland University; 2200 N. Squirrel Road, Rochester, MI 48309.

* cited by examiner

SYSTEM AND METHOD FOR TESTING TRUE STRESS AND TRUE STRAIN

BACKGROUND

Conventional engineering stress tests are often used for determining stress, strain, yield strength, tensile strength, fracture point, ductility, and other mechanical properties of parts and materials. These standard tests (per ASTM E8 and A370) do not take into account the "in test" reduction in cross sectional area as the specimen is stretched (a phenomenon called "necking") and only uses the original gage area for generation of the engineering stress-strain curve. "In test" measurement of the actual cross sectional area is of key importance in the calculation of the "true stress–true strain" curve where measurement of this reduced area (i.e. necked region) is difficult to consistently and accurately measure in real time all the way to the point of specimen failure.

Conventional stress and strain testing systems also only measure the area of the specimens using stationary tags and/or digital markers usually in a single direction or single measuring position. Hence, these systems fail to correctly adjust to the correct area as these tags cannot move and are not usually placed at the location of minimum area throughout the test. This results in significant errors in the calculation of the true stress–true strain curve for the specimen being tested.

SUMMARY

Embodiments of the present invention solve the above-mentioned problems and provide a distinct advance in the art of stress testing. More particularly, the present invention provides a testing system and method for determining true stress in which a minimum diameter of a specimen is determined over a plurality of points along the specimen to account for changes in location of maximum necking of the specimen.

An embodiment of the present invention is a true stress testing system for determining true stress of a specimen being subjected to an applied force. The system broadly comprising a force input machine, an imaging system, and a computer. The force input machine imparts a force on the specimen (e.g., a tensile force along a force axis). The imaging system includes a light source for projecting a light beam in a first direction at the specimen and a camera positioned on an opposite side of the specimen for receiving portions of the light beam not blocked by the specimen. A shadow image of the specimen is thus created via the camera. The computer may determine a minimum diameter of the specimen perpendicular to the first direction at a point in time over a plurality of points along the specimen via the shadow image. The computer can then account for changes in position of the minimum diameter along the specimen as the specimen is subjected to the force over time. A true stress of the specimen may then be determined according to the force applied to the specimen and the minimum diameter of the specimen perpendicular to the first direction at the point in time. Accounting for changes in the position of the minimum diameter along the specimen provides more accurate stress analysis when compared to theoretical stress, which does not take into account movement of the minimum diameter along the specimen.

Another embodiment of the present invention is a method of determining true stress of a specimen. The method includes positioning a specimen in a force input machine; aiming a light source at the specimen; aligning a camera with the light source on an opposite side of the specimen; projecting a light beam from the light source in a first direction so that at least some of the first light beam reaches the camera, receiving at least some of the light beam via the camera so as to create a shadow image of the specimen; and applying a force via the force input machine. A minimum diameter of the specimen perpendicular to the first direction at a point in time over a plurality of points along the specimen may be determined so that the computer accounts for changes in position of the minimum diameter along the specimen as the specimen is subjected to the force over a period of time. A true stress of the specimen may then be determined according to the force applied to the specimen and the minimum diameter of the specimen perpendicular to the first direction at the point in time.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

Figure 1:
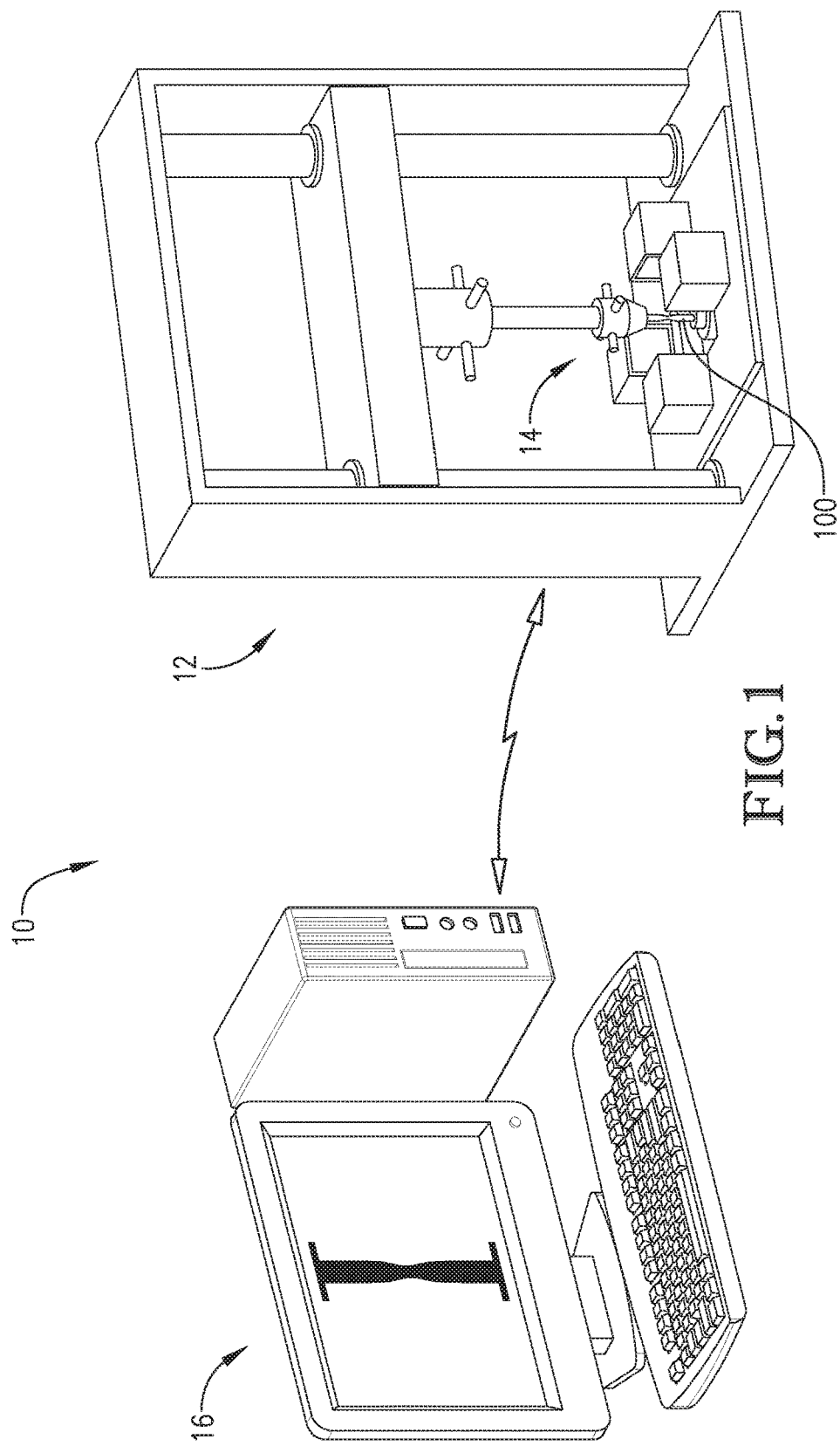
FIG. 1 is a perspective view of a true stress and true strain testing system constructed in accordance with an embodiment of the present invention.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

Turning to the drawing figures, a true stress and true strain testing system 10 constructed in accordance with an embodiment of the present invention is illustrated. The true stress and true strain system 10 determines true stress of a specimen 100 being subjected to an applied force. The specimen 100 may be a standard test piece for testing material properties, a part formed via conventional machining or molding or via additive manufacturing for testing part geometry or forming techniques, or any other test piece. The specimen 100 may have a round, rectangular, oval, or any other suitable cross section. As best shown in FIG. 1, the true stress and true strain testing system 10 broadly comprises a force input machine 12, an imaging system 14, and a computer 16.

Figure 2:
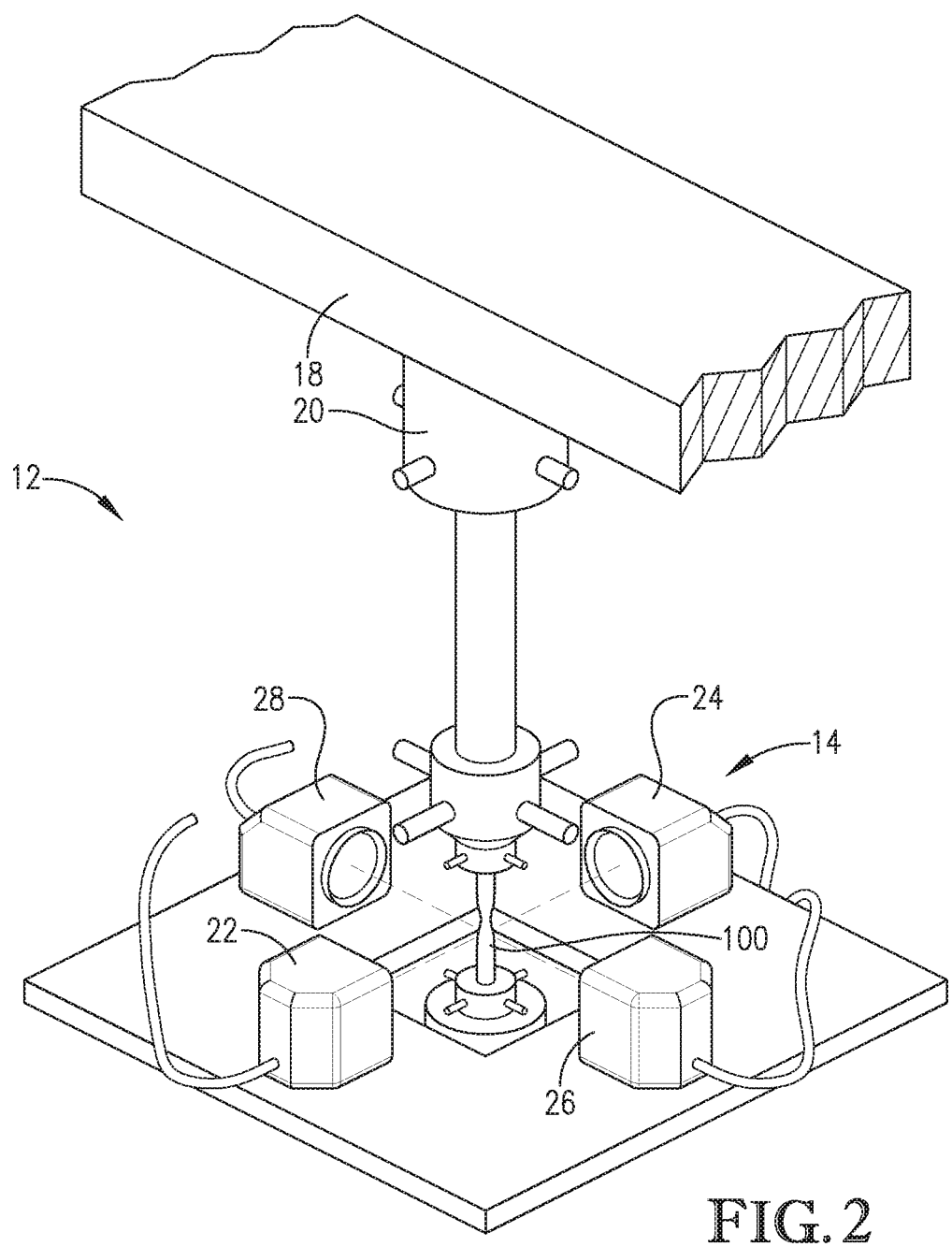
FIG. 2 is a perspective view of a force input machine and imaging system of the true stress and true strain testing system of FIG. 1.

The force input machine 12 applies a force to the specimen 100 and broadly includes a load frame 18 and a load cell 20, as shown in FIG. 2. The load frame 18 may include hydraulics, pneumatics, or other mechanical systems for applying the force to the specimen 100. The load cell 20 senses the amount of force exerted by the load frame 18. The force input machine 12 may also include an alignment head for allowing the specimen 100 to be manually or automatically aligned with components of the imaging system 14 and may include additional hydraulics, pneumatics, and spacers for effecting the alignment. The force may be a tensile or compression force applied along a force axis, a torsional force applied about the force axis, a bending force, or a combination of the above forces, as described in more detail below.

The imaging system 14 captures images of the specimen 100 and broadly includes a first light source 22 and a first camera 24. The imaging system 14 may also include a second light source 26, a second camera 28, and/or additional sensors as described below. The imaging system 14 may be mounted on an adjustable plate or may otherwise by adjustable for aligning the imaging system 14 with the specimen 100.

The first light source 22 produces a first imaging light beam and may be positioned facing the specimen 100 so that the first imaging light beam emitted from the first light source 22 is directed towards the specimen 100 in a first direction. Optionally, the first light source 22 may be positioned perpendicular to the force axis so that the first imaging light beam reaches the specimen 100 "head on". The first light source 22 may be a laser head (e.g., Keyence brand laser head) or any other light source. The first light source 22 may produce a laser beam or other focused light beam in a single electromagnetic wavelength or over a range of electromagnetic wavelengths.

The first camera 24 receives a portion of the first imaging light beam not blocked by the specimen 100 and may be aligned with the first light source 22 on an opposite side of the force axis. The first camera 24 may be a Keyence brand imaging camera or any other camera or sensor configured to detect directional light.

The second light source 26 produces a second imaging light beam and may be positioned facing the specimen 100 so that the second imaging light beam emitted from the second light source 26 is directed towards the specimen 100 in a second direction. That is, the second light source 26 may be angled from the first light source 22 so that the first imaging light beam and the second imaging light beam reach the specimen 100 in different directions. Optionally, the second light source 26 may be positioned perpendicular to the force axis so that the second imaging light beam reaches the specimen 100 "head on". In one embodiment, the second light source 26 is angled ninety degrees from the first light source 22 so that the first imaging light beam and the second imaging light beam reach the specimen 100 at ninety degree angles from each other. The second light source 26 may be a laser head (e.g., Keyence brand laser head) or any other light source. The second light source 26 may produce a laser beam or other focused light beam in a single electromagnetic wavelength or over a range of electromagnetic wavelengths.

The second camera 28 receives a portion of the second imaging light beam not blocked by the specimen 100 and may be aligned with the second light source 26 on an opposite side of the force axis. The second camera may be a Keyence brand imaging camera or any other camera or sensor configured to detect directional light.

Figure 3:
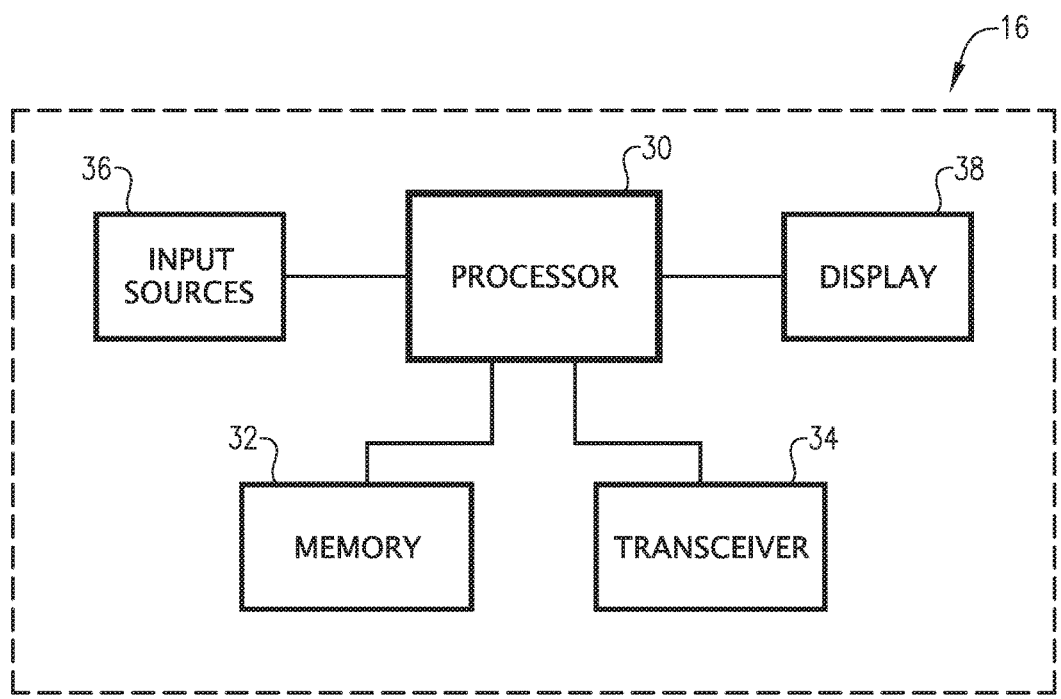
FIG. 3 is a block diagram showing certain components of a computer of the true stress and true strain testing system of FIG. 1.

The computer 16 determines true stress and true strain of the specimen 100 and broadly includes a processor 30, a memory 32, a transceiver 34, a plurality of inputs 36, and a display 38, as shown in FIG. 3. The computer 16 may be a desktop computer, laptop computer, tablet, smartphone, computer network, or any other computing device, system, or systems.

The processor 30 receives shadow images 102, 104 of the specimen 100 from the first camera 24 and the second camera 28 and determines true stress and true strain of the specimen based on the shadow images 102, 104 as described below. The processor 30 may include one or more circuit boards, memories, displays, inputs, and/or other electronic components.

The processor 30 may implement aspects of the present invention with one or more computer programs stored in or on computer-readable medium residing on or accessible by the processor. Each computer program preferably comprises an ordered listing of executable instructions for implementing logical functions in the processor 30. Each computer program can be embodied in any non-transitory computer-readable medium, such as the memory 32 (described below), for use by or in connection with an instruction execution system, apparatus, or device, such as a computer-based system, processor-containing system, or other system that can fetch the instructions from the instruction execution system, apparatus, or device, and execute the instructions.

The memory 32 may be any computer-readable non-transitory medium that can store the program for use by or in connection with the instruction execution system, apparatus, or device. The computer-readable medium can be, for example, but not limited to, an electronic, magnetic, optical, electro-magnetic, infrared, or semi-conductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM).

The transceiver 34 may transmit data and instructions between the force input machine 12, the imaging system 14, the computer 16, and other computers in the network. Alternatively, a wired or integrated setup may be used between these components.

The inputs 36 allow a user to activate and control the force input machine 12 and the imaging system 14 and manipulate data via the computer 16, and other computers in the network. The inputs 36 may comprise a keyboard, mouse, trackball, touchscreen, buttons, dials, virtual inputs, and/or a virtual reality simulator.

Figure 4:
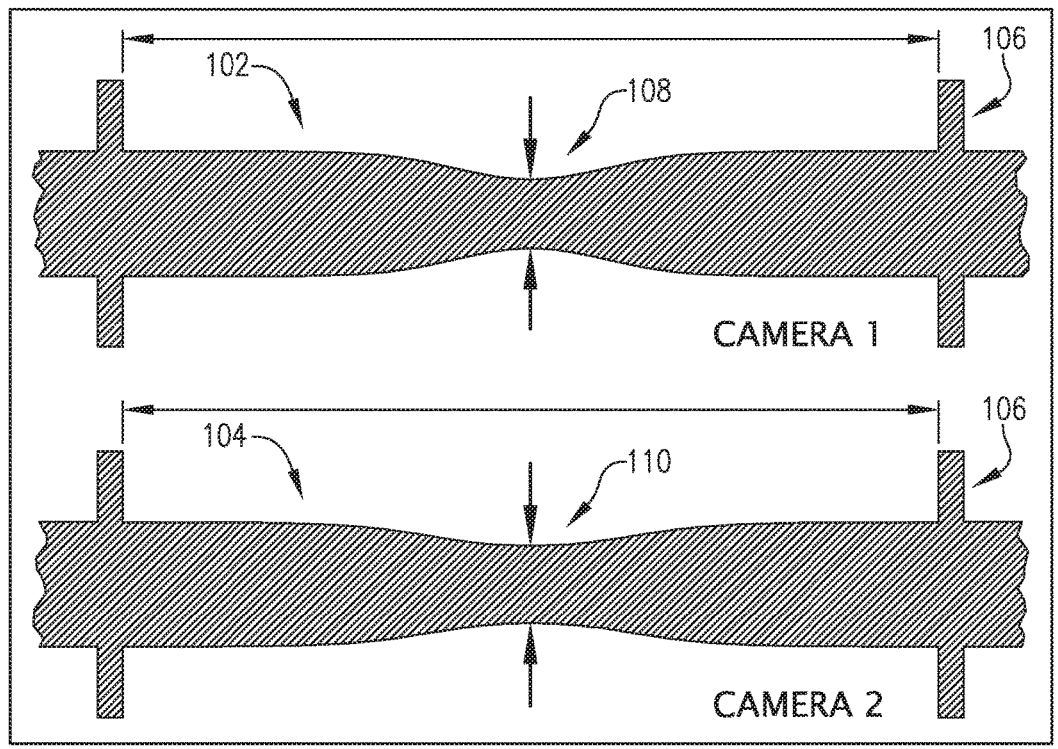
FIG. 4 shows shadow images generated via cameras of the true stress and true strain testing system.

The display 38 may present the shadow images 102, 104 of the specimen 100 (see FIG. 4), input force data, minimum diameter data (i.e., minimum widths or thicknesses), elongation data (i.e., elongation), metadata, computer options, stress plots (see FIG. 5), strain plots, and other information via a graphical user interface (GUI). The display 38 may also include image windows, data spreadsheets, virtual setup windows, and virtual inputs.

Use of the true stress and true strain testing system 10 will now be described in more detail. First, the specimen 100 may be positioned in or on the force input machine 12, as shown in block 200 of FIG. 6. The specimen 100 may be positioned such that a longitudinal axis of the specimen 100 is aligned with a force axis of the force input machine 12.

The first light source 22 may be positioned so that it faces the specimen 100, as shown in block 202. That is, the first light source 22 should be able to shine a first light beam towards the specimen 100 in a first direction.

The first camera 24 may then be aligned with the first light source 22 on an opposite side of the force axis, as shown in block 204. The first camera 24 should be positioned to receive portions of the first light beam from the first light source 22 that are not blocked by the specimen 100.

The second light source 26 may be positioned so that it faces the specimen 100 at an angle from the first light source 22, as shown in block 206. That is, the second light source 26 should be able to shine a second light beam towards the specimen 100 at an angle from the first light source 22 (i.e., in a different direction than the first light beam). In one embodiment, the second light source 26 may be positioned at a ninety degree angle from the first light source 22.

The second camera 28 may then be aligned with the second light source 26 on an opposite side of the force axis, as shown in block 208. The second camera 28 should be positioned to receive portions of the second light beam from the second light source 28 that are not blocked by the specimen 100.

Once the force input machine 12 and the imaging system 14 are set up, the specimen 100 may then be aligned or adjusted between the first light source 22 and the first camera 24 and between the second light source 26 and the second camera 28 via the adjustable alignment head of the force input machine 12, as shown in block 210. This will allow the first camera 24 and the second camera 28 to capture optimally framed shadow images 102, 104, as described below.

Optionally, one or more clips or other markers may be connected or attached to the specimen 100 near opposite ends of the specimen 100, as shown in block 212. The clips will provide reference points in the shadow images 102, 104 for elongation or other deformations of the specimen 100, as described below.

A first light beam may be projected from the first light source 22 towards the specimen 100 in a first direction (i.e., a first cross axis) during the period of time that the force is applied to the specimen 100, as shown in block 214. The first light beam may be continuous or may be pulsed according to a predetermined pulse rate (e.g., every twenty milliseconds or fewer).

Portions of the first light beam should be blocked by the specimen 100 while other portions of the first light beam should be received by the first camera 24, as shown in block 216. A first shadow image 102 of the specimen 100 may thus be created via the first camera 24. The first shadow image 102 may include clip shadows 106 of the clips connected to the specimen 100, which may be used for determining true strain, as described below.

A second light beam may also be projected from the second light source 26 towards the specimen 100 in a second direction (i.e., a second cross axis) during the period of time that the force is applied to the specimen 100, as shown in block 218. The second light beam may be continuous or may be pulsed according to a predetermined pulse rate (e.g., every twenty milliseconds or fewer).

Portions of the second light beam should be blocked by the specimen 100 while other portions of the second light beam should be received by the second camera 28, as shown in block 220. A second shadow image 104 of the specimen 100 may thus be created via the second camera 28. The second shadow image 104 may include clip shadows 106 of the clips connected to the specimen 100, which may be used for determining true strain, as described below.

The force input machine 12 may then be activated to apply a force to the specimen 100, as shown in block 222. The force may be a tensile force or compression force applied along a force axis, a torsional force applied about the force axis, a bending force, or a combination of one or more of the above forces. The force may be applied and increased in a linear or stepped pattern or at an increasing rate or a decreasing rate. The force may also be held at a steady amount for a predetermined period of time, cycled, ramped up and down, switched or gradually cycled between counter forces (e.g., switched or cycled between tensile and compression forces), such as for studying cyclic fatigue and/or creep testing, or any other force pattern. The force may be applied over a predetermined period of time or until the specimen 100 begins necking, begins fracturing, or fractures completely.

The specimen 100 will begin "necking" (i.e., narrowing in diameter along a portion of the specimen 100) from elongation due to tensile forces or otherwise deforming due to other types of forces applied to the specimen. The maximum stress on the specimen 100 will be felt where necking is greatest (i.e., where the specimen 100 has the smallest cross sectional area). However, the smallest cross sectional area may change positions along the specimen as viewed from the cameras 24, 28. For this reason, the minimum diameters 108, 110 of the specimen 100 may be determined for a range of points along the specimen, as described in more detail below.

Imaging masks may be used on the first and second shadow images 102, 104 for assisting the processor 30 in determining minimum diameters 108, 110 or minimum dimensions (explained in more detail below) and for tracking positions of and changes in the test specimen 100, as shown in block 224. Other imaging techniques and data manipulation techniques may also be used for simplifying the image and data analysis.

A minimum diameter 108 of the specimen perpendicular to the first direction may be determined at one or more points in time while the force is being applied to the specimen 100, as shown in block 226. This may be determined by measuring thicknesses of the first shadow image 102 at a number of points along the specimen 100 and identifying the smallest measured thickness. Note that for each minimum diameter determination, the smallest measured thickness may be located at different points along the specimen 100.

A minimum diameter 110 of the specimen perpendicular to the second direction may be determined at one or more points in time while the force is being applied to the specimen 100, as shown in block 228. This may be determined by measuring thicknesses of the second shadow image 104 at a number of points along the specimen 100 and identifying the smallest measured thickness. Note that for each minimum diameter determination, the smallest measured thickness may be located at different points along the specimen 100.

The minimum diameters 108, 110 described above may be determined at any point or points in time while the force is being applied to the specimen 100. In one embodiment, the minimum diameters 108, 110 may be determined continuously or every twenty milliseconds or fewer. It will be understood that the shadow images 102, 104 may be captured for these points in time while the minimum diameters 108, 110 are determined after the fact in a data analysis session.

Figure 5:
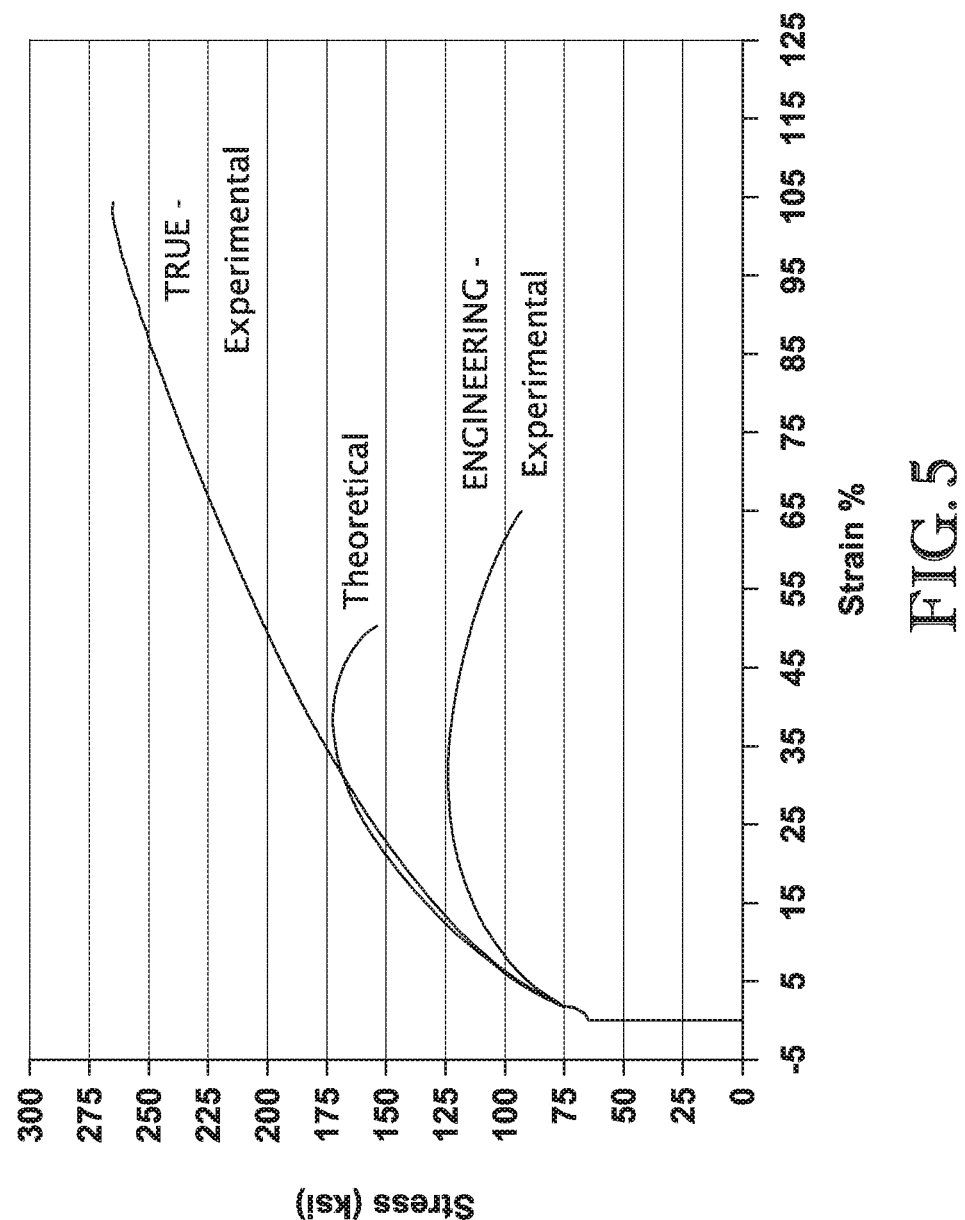
FIG. 5 is a stress plot comparing true stress determined via the true stress and true strain testing system with engineering stress and theoretical stress determined via conventional systems.

A true stress of the specimen 100 at a point in time may then be determined according to the amount of force applied to the specimen 100 at the point in time and a minimum cross sectional area of the specimen 100 as calculated from the minimum diameter 108 of the specimen 100 perpendicular to the first direction at the point in time and the minimum diameter 110 of the specimen 100 perpendicular to the second direction at the point in time (and/or the known cross sectional shape of the specimen 100, as shown in block 230. The calculated minimum cross sectional area of the specimen 100 may be an average of an area measurement based on the minimum diameter 108 in the first direction and an area measurement based on the minimum diameter 110 in the second direction. Alternatively, the calculated minimum cross sectional area may be a direct function of the minimum diameter 108 in the first direction and the minimum diameter 110 in the second direction such as for calculating an oval or rectangular shape. A true stress of the specimen 100 for a plurality of points in time or a period of time may similarly be determined by repeating the above steps for different points in time. The true stress may be plotted against time and/or against force to show a complete behavior of the specimen 100, as shown in FIG. 5. It will be understood that the true stress may be calculated as instantaneous load divided by instantaneous cross sectional area of the specimen 100. True strain may be calculated as the natural log of the instantaneous cross sectional area divided by the original cross sectional area or the natural log of the instantaneous length divided by the original length of the specimen 100.

Note that the minimum cross sectional area of the specimen 100 may not necessarily correspond to a point on the specimen 100 along the force axis at which both of the minimum diameters 108, 110 are located. For example, the first minimum diameter 108 may be so small at one point that the specimen 100 may have significant thickness as seen from the second direction yet still have a minimum cross sectional area at that point. That is, the minimum diameters 108, 110 may be located at different points along the specimen 100 for a single point in time. To account for this, the processor 30 may need to calculate cross sectional areas for a number of points along the force axis at a single point in time to determine the actual minimum cross sectional area at that point in time.

Figure 6:
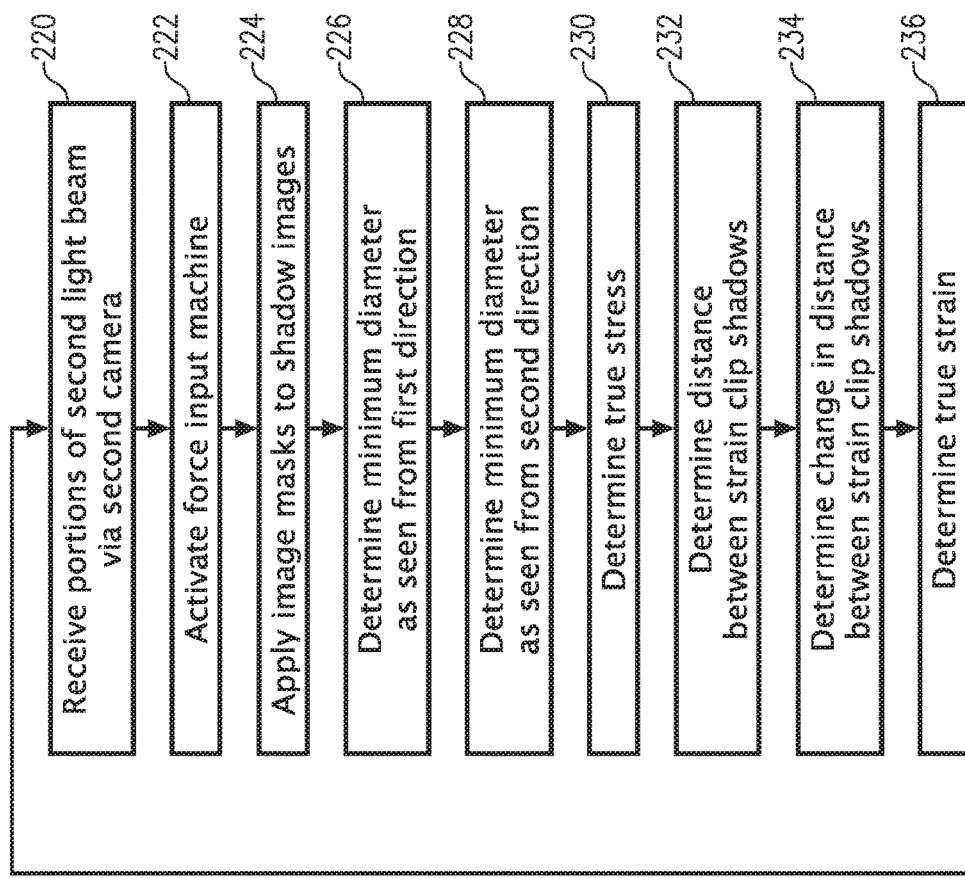
FIG. 6 is a flow diagram of steps in a method of determining true stress and true strain of a specimen.
Figure 6:
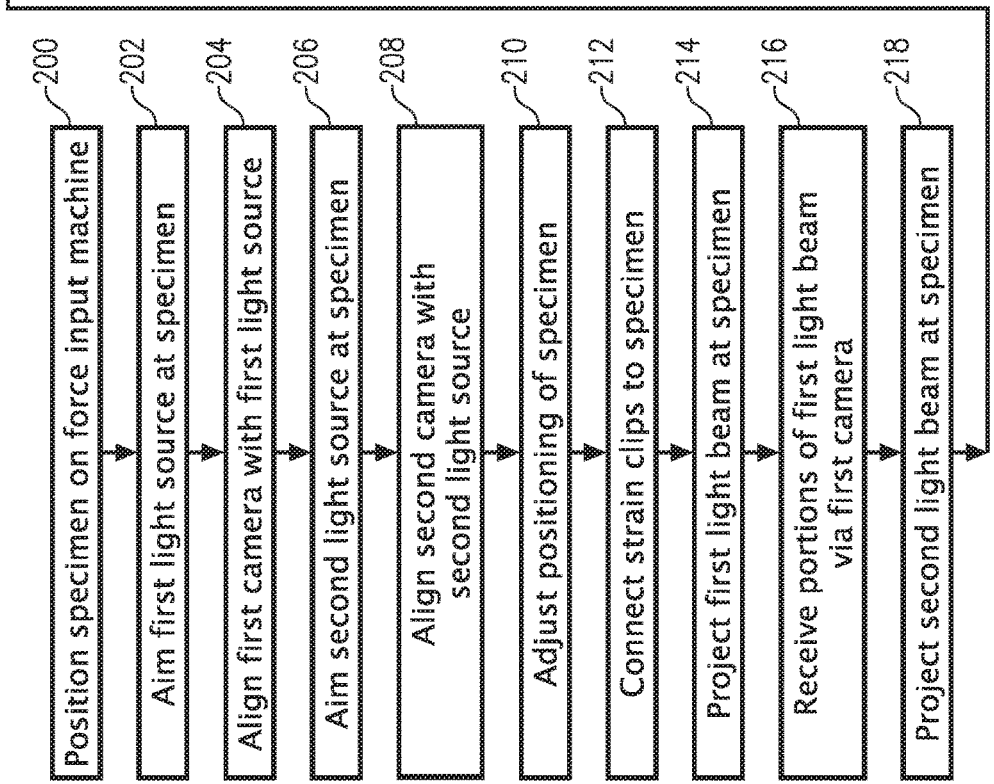

A distance between the clip shadows 106 in one or both of the shadow images 102, 104 at a plurality of points in time as the force is applied to the specimen 100 may be measured, as shown in block 232 of FIG. 6. The distance measured may be parallel to a force axis or force direction but may also be measured in other directions. An initial distance between the shadow clips 106 at an initial point in time may be used in determining true strain, as described below.

Changes in the distance between the clip shadows 106 from one point in time and another point in time may then be determined, as shown in block 234. The points in time may be subsequent points in time or may be start and end points.

A true strain may then be determined as a change in the distance between the clip shadows 106 divided by an initial distance, as shown in block 236. Alternatively, the true strain may be determined as a change in a minimum lateral dimension (diameter, width, or thickness) of the specimen 100 divided by an initial lateral dimension. The true strain may be plotted to show true strain over the period of time that the force is applied to the specimen 100.

The above-described true stress and true strain testing system 10 and method provide several advantages over conventional systems. For example, the true stress and true strain testing system 100 scans the entire gage length of the specimen and measures the actual minimum diameters 108, 110 of the specimen throughout the test. This provides improved stress analysis over theoretical stress because theoretical stress does not take into account changes in location of the minimum diameters 108, 110 of the specimen 100 (see FIG. 5). In contrast, conventional testing systems use reflective laser tags placed on the specimen. Unfortunately, these tags may not be placed on the region where the minimum dimension is located. These tags also cannot move as the location of the minimum dimension moves. This leads to much less accuracy and incorrect stress and strain curves. The true stress and true strain testing system 10 also provides more accurate results because minimum diameters 108, 110 as seen from two or more different directions are determined and incorporated into the true stress analysis. This allows for specimens having different cross sections (circular, oval, rectangular, etc.) to be more accurately analyzed. Indeed, the true stress and true strain testing system 10 allows for enhanced analysis of non-linear plastic behavior of additive manufactured materials, organic materials, metals, and other materials. Parts formed via additive manufacturing having elaborate and complicated geometries in particular benefit from the enhanced analysis provided by the true stress and true strain testing system 10. Note also that the true stress and true strain testing system 10 captures more data points while the specimen is subjected to a test force than can be performed by hand.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A system for testing true stress of a specimen, the system comprising:
    a force input machine for imparting a force on the specimen;

an imaging system comprising:
  a first light source configured to project a first light beam at the specimen in a first direction; and
  a first camera aligned with the first light source on an opposite side of the specimen such that the first camera receives a first shadow image of the specimen;
a computer having a processor configured to:
  determine a minimum diameter of the specimen perpendicular to the first direction at a plurality of points in time over a plurality of points along the specimen such that the processor accounts for changes in position of the minimum diameter along the specimen as the specimen is subjected to the force over a period of time; and
  determine a true stress according to the force applied to the specimen at the point in time and the minimum diameter of the specimen perpendicular to the first direction at the point in time; and
a plurality of clips each being configured to cast a clip shadow on the first camera, wherein the processor determines a true strain of the specimen based on a change in spacing between the clip shadows and generates an image mask for simplifying analysis of the first shadow image of the specimen.

2. The system of claim 1, wherein the imaging system further comprises:
  a second light source angled from the first light source and configured to project a second light beam at the specimen in a second direction; and
  a second camera aligned with the second light source on an opposite side of the specimen such that the second camera receives a second shadow image of the specimen, wherein the computer processor is further configured to determine a minimum diameter of the specimen perpendicular to the second direction at the point in time, the true stress being determined according to the minimum diameter of the specimen perpendicular to the first direction at the plurality of points in time and the minimum diameter of the specimen perpendicular to the second direction at the plurality of points in time.

3. The system of claim 1, wherein the first light source and the second light source are angled ninety degrees from each other and the first camera and the second camera are angled ninety degrees from each other.

4. The system of claim 1, wherein the processor is configured to determine the minimum diameter at least every twenty milliseconds.

5. The system of claim 1, wherein the processor is configured to account for whether the specimen has a round cross section or a rectangular cross section in determining the true stress.

6. The system of claim 1, wherein the force input machine comprises an adjustable alignment head for aligning the test specimen with the first light source and the first camera.

7. A system for testing true stress and true strain of a specimen, the system comprising:
  a force input machine for imparting a force on the specimen along a force axis and increases the force in a selected one of a linear rate, an increasing rate, a decreasing rate, and a stepped pattern, the force input machine including an adjustable alignment head for aligning the test specimen;
  an imaging system mounted on an adjustable plate for aligning with the specimen, the imaging system comprising:
    a first light source positioned perpendicular to the force axis and configured to project a first light beam at the specimen in a first direction;
    a first camera configured to be aligned with the first light source on an opposite side of the specimen such that the first camera receives a first shadow image of the specimen;
    a second light source positioned perpendicular to the force axis and angled ninety degrees from the first light source, the second light source being configured to project a second light beam at the specimen in a second direction; and
    a second camera aligned with the second light source on an opposite side of the specimen such that the second camera receives a second shadow image of the specimen;
  a plurality of clips configured to be connected to the specimen, each clip being configured to cast a clip shadow on at least one of the first camera and the second camera; and
  a computer having a processor configured to:
    determine a minimum diameter of the specimen perpendicular to the first direction at a plurality of points in time over a period of time while the force is being applied to the specimen;
    determine a minimum diameter of the specimen perpendicular to the second direction for the plurality of points in time over the period of time;
    determine a true stress of the specimen according to the force applied to the specimen at the plurality of points in time and the minimum diameters of the specimen at the plurality of points in time;
    determine a true strain of the specimen based on a change in spacing between the clip shadows for the plurality of points in time; and
    generate an image mask for simplifying analysis of the first shadow image and the second shadow image of the specimen.

* * * * *